United States Patent [19]

Ushio et al.

[11] Patent Number: 5,597,929
[45] Date of Patent: Jan. 28, 1997

[54] PRODUCTION PROCESS OF 2-(TETRAZOL-5-YL)-4-OXO-4H-BENZOPYRAN

[75] Inventors: Hideki Ushio, Takatsuki, Japan; Takayuki Higashii, Irvington, N.Y.

[73] Assignee: Sumitomo Chemical Co., Ltd., Osaka, Japan

[21] Appl. No.: 601,029

[22] PCT Filed: Jun. 23, 1995

[86] PCT No.: PCT/JP95/01261

§ 371 Date: Feb. 23, 1996

§ 102(e) Date: Feb. 23, 1996

[87] PCT Pub. No.: WO96/00225

PCT Pub. Date: Jan. 4, 1996

[30] Foreign Application Priority Data

Jun. 23, 1994 [JP] Japan ..................... 6-141759

[51] Int. Cl.⁶ .................................................. C07D 405/04
[52] U.S. Cl. .................................. 548/253; 548/101
[58] Field of Search .................................. 548/253, 101

[56] References Cited

FOREIGN PATENT DOCUMENTS

| | | |
|---|---|---|
| 1356379 | 6/1974 | European Pat. Off. . |
| 1362782 | 8/1974 | European Pat. Off. . |
| 0104018 | 3/1984 | European Pat. Off. . |
| 59-76062 | 4/1984 | Japan . |
| 5-279305 | 10/1993 | Japan . |
| WO94/12492 | 6/1994 | WIPO . |

*Primary Examiner*—David B. Springer
*Attorney, Agent, or Firm*—Birch, Stewart, Kolasch & Birch, LLP

[57] ABSTRACT

There is disclosed a process for producing a 2-(tetrazol-5-yl)-4-oxo-4H-benzopyran of general formula (1):

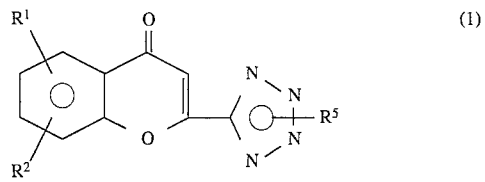

which comprises reacting a hydroxyacetophenone of general formula (2):

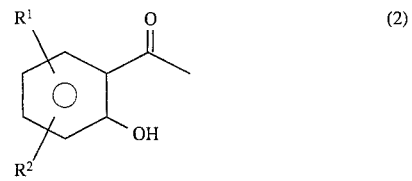

with a tetrazole compound of general formula (3):

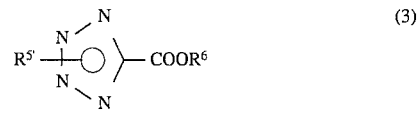

in the presence of a base in a solvent composed mainly of at least one selected from hydrocarbons, halogenated hydrocarbons and alcohols, and then treating the reaction mixture under acidic conditions.

17 Claims, No Drawings

PRODUCTION PROCESS OF 2-(TETRAZOL-5-YL)-4-OXO-4H-BENZOPYRAN

This application is a 371 of PCT/JP95/01261 filed Jun. 23, 1995.

1. Field of Invention

The present invention relates to production processes of 2-(tetrazol-5-yl)-4-oxo-4H-benzopyrans which are useful as pharmaceuticals or intermediates thereof.

2. Prior Art 2-(Tetrazol-5-yl)-4-oxo-4H-benzopyrans of general formula (1):

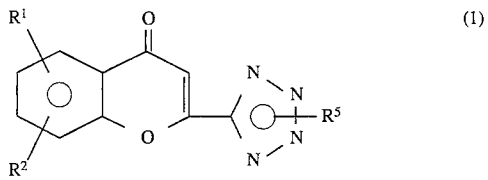

wherein $R^1$ and $R^2$ are the same or different and are a hydrogen atom, a hydroxy group, a halogen atom, a $C_1$–$C_{20}$ alkyl group, a $C_1$–$C_{20}$ alkoxy group, an $R^3$CONH group or a nitro group, in which $R^3$ is a $C_1$–$C_{20}$ alkyl group optionally substituted with an aryl group, or a phenyl group optionally substituted with $R^4$; $R^4$ is a $C_1$–$C_{20}$ alkyl group optionally substituted with an aryl group, or a $C_1$–$C_{20}$ alkoxy group optionally substituted with an aryl group; $R^5$ is a hydrogen atom, an alkyl or alkenyl group optionally substituted with an electron withdrawing group, an alkyl group substituted with 1 to 3 aryl groups, an alkoxycarbonyl group optionally substituted with an aryl group, an aryloxycarbonyl group, an alkoxymethyl group, a trialkyl tin group, a triaryl tin group or a trialkylsilyl group, in which the term "aryl group" or "aryl" means a phenyl group optionally substituted with a group selected from an alkyl group, an alkoxy group or a halogen atom, are compounds which are useful, for example, as antiasthmatics or intermediates thereof.

As a production process of 2-(tetrazol-5-yl)-4-oxo-4H-benzopyran (1), there has been known the following process which is disclosed, for example, in Journal of Medicinal Chemistry, 1972, 15, p.865.

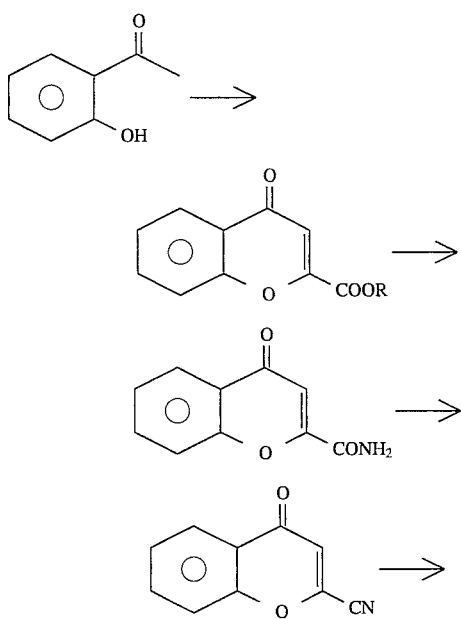

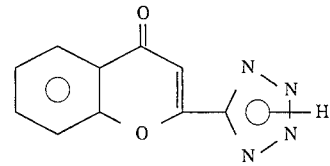

As a production process of 2-(tetrazol-5-yl)-4-oxo-4H-benzopyran (1) with a substituent introduced on the tetrazole ring, the following process is disclosed, for example, in publications GB-A1362782 and GB-A1356379.

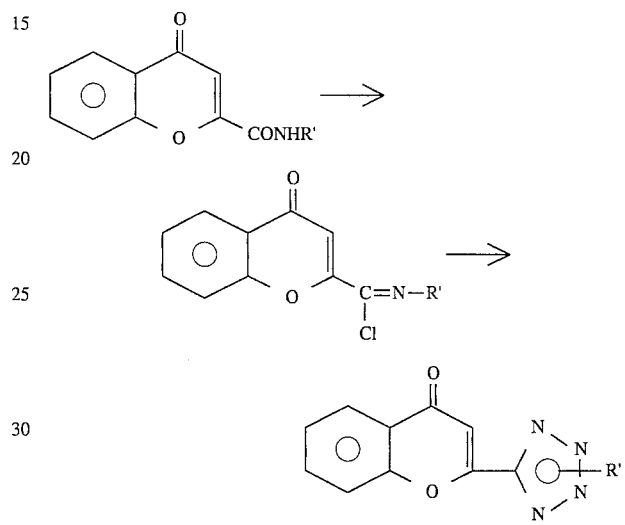

However, this process requires an additional reaction in the following step to obtain the above starting material compound from hydroxyacetophenone.

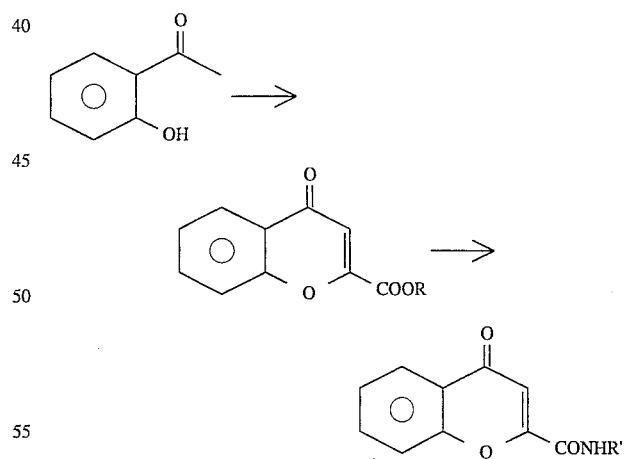

Therefore, these processes are complicated because of their involving many reaction steps, and they cannot attain satisfactory yield.

As a production process of a compound corresponding to 2-(tetrazol-5-yl)-4-oxo-4H-benzopyran (1) wherein substituent $R^5$ is a hydrogen atom, there is disclosed the following process, for example, in publication WO94/12492.

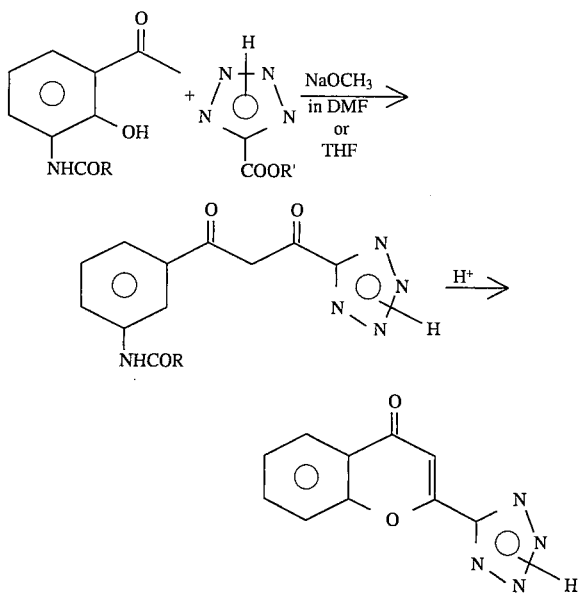

In the process described therein, tetrahydrofuran or N,N-dimethylformamide is used as the reaction solvent. When this process is applied to the production on an industrial scale, the use of such a solvent is not preferred from the viewpoint of its cost, safety, and difficulty in solvent recovery.

OBJECTS OF THE INVENTION

An object of the present invention is to provide a process for producing 2-(tetrazol-5-yl)-4-oxo-4H-benzopyrans (1) in an industrially favorable manner, which are useful as drug substances or pharmaceutical intermediates. This and other objects and excellent advantages will be understood from the following description.

SUMMARY OF THE INVENTION

The present inventors have intensively studied to solve the above problems of the prior art. As a result, they have found that the reaction can be smoothly effected even in an industrially favorable solvent by using, as a tetrazole compound, those having a substituent on the tetrazole ring and further that 2-(tetrazol-5-yl)-4-oxo-4H-benzopyrans can be produced in an industrially favorable manner, and they have made further studies, thereby completing the present invention.

Thus, the present invention provides a process for producing 2-(tetrazol-5-yl)-4-oxo-4H-benzopyran (1), which comprises reacting a hydroxyacetophenone of general formula (2):

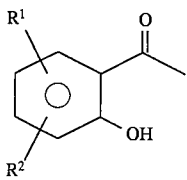

wherein $R^1$ and $R^2$ are as defined above, with a tetrazole compound of general formula (3):

wherein $R^{5'}$ is $R^5$ which is not a hydrogen atom, $R^6$ is a lower alkyl group optionally substituted with a halogen atom, and $R^5$ is as defined above, in the presence of a base in a solvent composed mainly of at least one selected from hydrocarbons, halogenated hydrocarbons and alcohols, and then treating the reaction mixture under acidic conditions.

DETAILED DESCRIPTION OF THE INVENTION

The present invention will be further illustrated below.

In the production process of the present invention, hydroxyacetophenone (2) and tetrazole compound (3) are first reacted in the presence of a base in at least one solvent selected from hydrocarbons, halogenated hydrocarbons and alcohols to give diketone compound (4) of general formula (4):

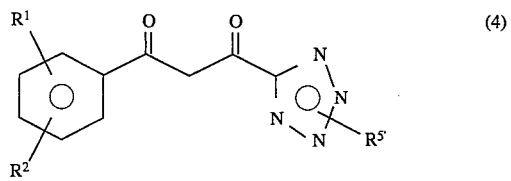

wherein $R^1$, $R^2$ and $R^{5'}$ are as defined above.

The diketone compound (4) usually includes two types of tautomers, which are represented by the term "diketone compound (4)" throughout this specification.

In the above reaction, the use of a tetrazole compound having substituent $R^{5'}$ introduced on the tetrazole ring makes it possible to obtain diketone compound (4) with high efficiency even when industrially favorable solvents, which are inexpensive and less dangerous because of less formation of peroxide as compared with tetrahydrofuran, are used, such as hydrocarbons, halogenated hydrocarbons and alcohols. $R^1$ and $R^2$ in the hydroxyacetophenone (2) are the same or different and are a hydrogen atom; a hydroxy group; a halogen atom such as chlorine or bromine atom; a $C_1$–$C_{20}$ alkyl group such as methyl or ethyl group; a $C_1$–$C_{20}$ alkoxy group such as methoxy or ethoxy group; an $R^3$CONH group, in which $R^3$ is a $C_1$–$C_{20}$ alkyl group optionally substituted with an aryl group, such as methyl, ethyl, benzyl, phenetyl, methylbenzyl, methoxybenzyl or chlorobenzyl group, or a phenyl group optionally substituted with $R^4$; $R^4$ is a $C_1$–$C_{20}$ alkyl group optionally substituted with an aryl group, such as methyl, ethyl, benzyl, phenetyl, phenylbutyl, methylbenzyl, methoxybenzyl or chlorobenzyl group, or a $C_1$–$C_{20}$ alkoxy group optionally substituted with an aryl group, such as methoxy, ethoxy, benzyloxy, phenylbutoxy, phenylethoxy, methylbenzyloxy, methoxybenzyloxy or chlorobenzyloxy group; or a nitro group. The term "aryl group" means a phenyl group optionally substituted with a group selected from an alkyl group usually containing 1 to 10 carbon atoms, such as methyl, ethyl, propyl or butyl group, an alkoxy group usually containing 1 to 10 carbon atoms, such as methoxy, ethoxy, propoxy or butoxy group, or a halogen atom such as chlorine or bromine atom.

Typically, there can be mentioned, for example, 2-hydroxyacetophenone compounds such as 2-hydroxyacetophenone, 2,4-dihydroxyacetophenone, 2,6-dihydroxyacetophenone, 5-chloro-2-hydroxyacetophenone, 5-bromo-2- hydroxyacetophenone, 4-methyl-2-hydroxyacetophenone, 5-methyl-2-hydroxyacetophenone, 5-ethyl-2-hydroxyacetophenone, 5-isopropyl-2-hydroxyacetophenone, 5-t-butyl-2-hydroxyacetophenone, 5-octyl-2-hydroxyacetophenone, 5-octadecyl-2-hydroxyacetophenone, 4-methoxy-2-hydroxyacetophenone, 4-ethoxy-2-hydroxyacetophenone, 4-isopropoxy-2-hydroxyacetophenone, 4-isopropoxy-2-hydroxyacetophenone, 4-octyloxy-2-hydroxyacetophenone, 4-octadecyloxy-2-hydroxyacetophenone, 3-acetylamino-2-hydroxyacetophenone, 5-acetylamino-2-hydroxyacetophenone, 3-propionylamino-2-hydroxyacetophenone, 5-propionylamino-2-hydroxyacetophenone, 3-nonanoylamino-2-hydroxyacetophenone, 5-nonanoylamino-2-hydroxyacetophenone, 3-hexadecanoylamino-2-hydroxyacetophenone, 5-hexadecanoylamino-2-hydroxyacetophenone, 3-phenylacetylamino-2-hydroxyacetophenone, hydroxyacetophenone, 5-phenylacetylamino-2-hydroxyacetophenone, 3-(3-phenylpropionyl)amino-2-hydroxyacetophenone, 5-(3-propionyl)amino-2-hydroxyacetophenone, 3-(9-phenylnonanoyl)amino-2-hydroxyacetophenone, 5-(9-phenylnonanoyl)amino-2-hydroxyacetophenone, 3-(4-methoxyphenyl)acetylamino-2-hydroxyacetophenone, 5-(4-methoxyphenyl)acetylamino-2-hydroxyacetophenone, 3-(4-chlorophenyl)acetylamino-2-hydroxyacetophenone, 5-(4-chlorophenyl)acetylamino-2-hydroxyacetophenone, 3-(3-chlorophenyl)acetylamino-2-hydroxyacetophenone, 5-(3-chlorophenyl)acetylamino-2-hydroxyacetophenone, 3-(2-chlorophenyl)acetylamino-2-hydroxyacetophenone, 5-(2-chlorophenyl)acetylamino-2-hydroxyacetophenone, 3-benzoylamino-2-hydroxyacetophenone, 5-benzoylamino-2-hydroxyacetophenone, 3-(4-methylbenzoyl)amino-2-hydroxyacetophenone, 5-(4-methylbenzoyl)amino-2-hydroxyacetophenone, 3-(4-ethylbenzoyl)amino-2-hydroxyacetophenone, 5-(4-ethylbenzoyl)amino-2-hydroxyacetophenone, 3-(4-butylbenzoyl)amino2-hydroxyacetophenone, 5-(4-butylbenzoyl)amino-2-hydroxyacetophenone, 3-(2-benzylbenzoyl)amino-2-hydroxyacetophenone, 5-(2-benzylbenzoyl)amino-2-hydroxyacetophenone, 3-[4-(3-phenylpropyl)benzoyl]amino-2-hydroxyacetophenone, 5-[4-(3-phenylpropyl)benzoyl]amino-2-hydroxyacetophenone, 3-[4-(4-phenylbutyl)benzoyl]amino-2-hydroxyacetophenone, 5-[4-(4-phenylbutyl)benzoyl]amino-2-hydroxyacetophenone, 3-[4-(4-methylbenzyl)benzoyl]amino-2-hydroxyacetophenone, 3-[4-(4-methoxybenzyl)benzoyl]amino-2-hydroxyacetophenone, 3-[4-(4-chlorobenzyl)benzoyl]amino-2-hydroxyacetophenone, 3-(4-methoxybenzoyl)amino-2-hydroxyacetophenone, 5-(4-methoxybenzoyl)amino-2-hydroxyacetophenone, 3-(4-ethoxybenzoyl)amino-2-hydroxyacetophenone, 5-(4-ethoxybenzoyl)amino-2-hydroxyacetophenone, 3-(4-propoxybenzoyl)amino-2-hydroxyacetophenone, 5-(4-propoxybenzoyl)amino-2-hydroxyacetophenone, 3-(4-butoxybenzoyl)amino-2-hydroxyacetophenone, 5-(4-butoxybenzoyl)amino-2-hydroxyacetophenone, 3-[4-(1,1-dimethylmethoxy)benzoyl]amino-2-hydroxyacetophenone, 5-[4-(1,1-dimethylmethoxy)benzoyl]amino-2-hydroxyacetophenone, 3-[4-(1,1,1-trimethylmethoxy)benzoyl]amino-2-hydroxyacetophenone, 5-[4-(1,1,1-trimethylmethoxy)benzoyl]amino-2-hydroxyacetophenone, 3-[4-(benzyloxy)benzoyl]amino-2-hydroxyacetophenone, 3-[4-(2-phenylethoxy)benzoyl]amino-2-hydroxyacetophenone, 3-[4-(3-phenylbutoxy)benzoyl]amino-2-hydroxyacetophenone, 5-[4-(3-phenylbutoxy))benzoyl]amino-2-hydroxyacetophenone, 3-[4-(4-phenylbutoxy)benzoyl]amino-2-hydroxyacetophenone, 5-[4-(4-phenylbutoxy)benzoyl]amino-2-hydroxyacetophenone, 3-[4-(8-phenyloctyloxy)benzoyl]amino-2-hydroxyacetophenone, 5-[4-(8-phenyloctyloxy)benzoyl]amino-2-hydroxyacetophenone, 3-[4-(4-methylbenzyloxy)benzoyl]amino-2-hydroxyacetophenone, 3-[4-(4-methoxybenzyloxy)benzoyl]amino-2-hydroxyacetophenone, 3-[4-(4-chlorobenzyloxy)benzoyl]amino-2-hydroxyacetophenone, 3-nitro-2-hydroxyacetophenone, 5-nitro-2-hydroxyacetophenone, 5-chloro-3-nitro-2-hydroxyacetophenone and 5-bromo-3-nitro-2-hydroxyacetophenone.

As the $R^5$ in the tetrazole compound (3), there can be mentioned alkyl groups usually containing 1 to 10 carbon atoms and optionally substituted with an electron withdrawing group, such as methyl, ethyl, propyl, cyanoethyl, methoxycarbonylethyl, ethoxycarbonylethyl, vinyl and 3-ethoxycarbonylpropenyl groups; alkyl groups usually containing 7 to 30 carbon atoms and substituted with 1 to 3 aryl groups, such as benzyl, phenetyl, phenylbutyl, methylbenzyl, methoxybenzyl, nitrobenzyl, chlorobenzyl, diphenylmethyl and triphenylmethyl (trityl) groups; alkoxycarbonyl groups usually containing 2 to 10 carbon atoms and optionally substituted with an aryl group, such as methoxycarbonyl, ethoxycarbonyl, t-butoxycarbonyl, propoxycarbonyl and benzyloxycarbonyl groups; aryloxycarbonyl groups usually containing 7 to 20 carbon atoms, such as phenoxycarbonyl, methylphenoxycarbonyl, methoxyphenoxycarbonyl and chlorophenoxycarbonyl groups; alkoxymethyl groups usually containing 2 to 10 carbon atoms, such as methoxymethyl, ethoxymethyl, propoxymethyl and butoxymethyl groups; trialkyl tin groups usually containing 3 to 20 carbon atoms, such as trimethyl tin and triethyl tin groups; triaryl tin groups usually containing 18 to 30 carbon atoms, such as triphenyl tin group; or trialkylsilyl groups usually containing 3 to 20 carbon atoms, such as trimethylsilyl and triethylsilyl groups, in which the term "aryl group" or "aryl" means a phenyl group optionally substituted with an alkyl group usually containing 1 to 10 carbon atoms, such as methyl, ethyl, propyl or butyl group, an alkoxy group usually containing 1 to 10 carbon atoms, such as methoxy, ethoxy, propoxy or butoxy group, or a halogen atom such as chlorine or bromine atom. As the $R^6$, there can be mentioned lower alkyl groups usually containing 1 to 4 carbon atoms, such as methyl, ethyl, propyl and butyl groups.

Typically, there can be mentioned, for example, N-substituted tetrazolecarboxylates such as ethyl (N-methyltetrazole)-5-carboxylate, ethyl (N-ethyltetrazole)-5-carboxylate, ethyl (N-t-butyltetrazole)-5-carboxylate, ethyl (N-cyclohexyltetrazole)-5-carboxylate, ethyl (N-octyltetrazole)-5-carboxylate, ethyl (N-vinyltetrazole)-5-carboxylate, ethyl [N-(2-chloroethyl)tetrazole]-5-carboxylate, ethyl [N-(2-cyanoethyl)tetrazole]-5-carboxylate, ethyl [N-(2-methoxycarbonylethyl)tetrazole]-5-carboxylate, ethyl [N-(2-ethoxycarbonylethyl)tetrazole]-5-carboxylate, ethyl [N-(1-ethoxyethyl)tetrazole]-5-carboxylate, ethyl [N-[2-(2'-pyridyl)ethyl]tetrazole]-5-carboxylate, ethyl (N-benzyltetrazole)-5-carboxylate, ethyl [N-(4-methoxybenzyl)tetrazole]-5-carboxylate, ethyl [N-(p-chlorobenzyl)tetrazole]-5-carboxylate, ethyl [N-(p-bromobenzyl)tetrazole]-5-carboxylate, ethyl [N-(o-nitrobenzyl)tetrazole]-5-carboxylate, ethyl [N-(p-nitrobenzyl)tetrazole]-5-carboxylate, ethyl [N-(p-chloro-2-nitrobenzyl)tetrazole]-5-carboxylate, ethyl [N-(o-aminobenzyl)tetrazole]-5-carboxylate, ethyl [N-(p-chloro-o-aminobenzyl)tetrazole]-5-carboxylate, ethyl [N-(5-chloro-2-aminobenzyl)tetrazole]-5-carboxylate, ethyl [N-(p-methyl-o-aminobenzyl)tetrazole]-5-carboxylate, ethyl [N-(2,4-dichlorobenzyl)tetrazole]-5-carboxylate, ethyl (N-benzylhydryltetrazole)-5-carboxylate, ethyl (N-trityltetrazole)-5-carboxylate, ethyl [N-[(4-methoxyphenyl)diphenylmethyl]tetrazole]-5-carboxylate, ethyl (N-ethoxycarbonyltetrazole)-5-carboxylate, methyl (N-methoxycarbonyltetrazole)-5-carboxylate, ethyl (N-tertiary-butoxycarbonyltetrazole)-5-carboxylate, methyl (N-tertiary-butoxycarbonyltetrazole)-5-carboxylate, ethyl (N-benzyloxycarbonyltetrazole)-5-carboxylate, methyl (N-benzyloxycarbonyltetrazole)-5-carboxylate, ethyl [N-(2-phenyl)ethoxycarbonyltetrazole]-5-carboxylate, [N-(2-trimethylsilyl)ethoxycarbonyltetrazole]-5-carboxylate, ethyl (N-allyloxycarbonyltetrazole)-5-carboxylate, ethyl (N-vinyloxycarbonyltetrazole)-5-carboxylate, ethyl (N-methoxymethyltetrazole)-5-carboxylate, ethyl (N-ethoxymethyltetrazole)-5-carboxylate, ethyl (N-butoxymethyltetrazole)-5-carboxylate, ethyl (N-trimethylsilyltetrazole)-5-carboxylate, ethyl (N-t-butyldimethylsilyltetrazole)-5-carboxylate, ethyl (N-trimethyl tin tetrazole)-5-carboxylate, ethyl (N-tributyl tin tetrazole)-5-carboxylate, and ethyl (N-triphenyl tin tetrazole)-5-carboxylate. These can readily be synthesized by the process, for example, as described in Journal of Medicinal Chemistry, 1986, 29, pp.538–549.

The amount of tetrazole compound (3) to be used is usually from about 1 to 20 moles, preferably from about 1 to 10 moles, relative to hydroxyacetophenone (2).

As the base, there can be mentioned, for example, alkali metal alcoholates such as sodium methylate, sodium ethylate and potassium t-butylate, hydrides such as sodium hydride and potassium hydride, and alkyl lithium such as methyl lithium and butyl lithium. From the viewpoint of operation environment, hazard protection and safety, alkali metal alcoholates and hydrides are preferred with alkali metal alcoholates being more preferred. In practice, it is preferred that alkali metal alcoholates are used as the corresponding alcohol solutions and alkyl lithium is used as a hydrocarbon solution.

The amount of base to be used is usually from about 1 to 30 moles, preferably from about 1 to 10 moles, relative to hydroxyacetophenone (2).

The solvent used in the reaction is composed mainly of at least one of the hydrocarbons, halogenated hydrocarbons and alcohols in an amount of at least 50% by weight, preferably at least 80% by weight, based on the total weight of the solvent, and more preferably, it contains substantially only hydrocarbons, halogenated hydrocarbons and/or alcohols. There can be mentioned, for example, hydrocarbons such as benzene, toluene and hexane, halogenated hydrocarbons such as dichloromethane, dichloroethane and chlorobenzene, alcohols such as methanol and ethanol, and mixtures thereof.

From the viewpoint of ease in the solvent recovery and cost, toluene, xylene, chlorobenzene, dichlorobenzene, methanol and ethanol are preferred with toluene, chlorobenzene and methanol being more preferred. As the other component used in the solvent, there can be mentioned ethers, nitriles, amides and sulfoxides. The amount of solvent to be used, although it is not particularly limited, is usually from about 1 to 200 times as much as the weight of hydroxyacetophenone (2).

The reaction temperature is usually 200° C. or lower, preferably −50° to 150° C. or up to the boiling point of the solvent.

The proceeding of the reaction can readily be monitored by an analytical method such as liquid chromatography. Usually, disappearance of hydroxyacetophenone (2) can be considered as the end point of the reaction.

After completion of the reaction, diketone compound (4) can be isolated, for example, by filtration after neutralization with an acid such as sulfuric acid, hydrochloric acid, methanesulfonic acid, hydrobromic acid or acetic acid; however, the reaction mixture can usually be used as such in the subsequent reaction.

The treatment of diketone compound (4) under acidic conditions gives 2-(tetrazol-5-yl)-4-oxo-4H-benzopyran (1).

As described above, diketone compound (4) can be used in isolated form; however, the above reaction mixture is usually used as such. Accordingly, the solvent used in the preceding step can be used as such. A solvent to be used may be different from the solvent used in the preceding step, in which case it is preferably compatible with the acid used.

In the above reaction, the term "acidic conditions" means the conditions that the reaction system is leaned from the neutral side to the acidic side, and such conditions can usually be achieved by addition of an acid.

As such an acid, sulfuric acid, hydrochloric acid, nitric acid, methanesulfonic acid, trifluoromethanesulfonic acid, acetic acid, trifluoroacetic acid or hydrobromic acid is used alone or in admixture. The amount thereof is not particularly limited, so long as the above acidic conditions are satisfied; it is usually from 1.1 to 100 moles, preferably 1.1 to 50 moles, relative to the base used, when the above reaction mixture is used as such, or it is reduced by subtraction of 1 mole from the above amount, when diketone compound (4) is used in isolated form.

In the case of diketone compound (4) wherein $R^{5'}$ is a group liable to be eliminated under acidic conditions, such as 4-methoxybenzyl, trityl or methoxymethyl group, elimination of $R^{5'}$ occurs with ring-closing reaction to give 2-(tetrazol-5-yl)-4-oxo-4H-benzopyran (1) wherein $R^5$ is a hydrogen atom.

In the case of diketone compound (4) wherein $R^{5'}$ is not eliminated, a 2-(tetrazol-5-yl)-4-oxo-4H-benzopyran of general formula (1'):

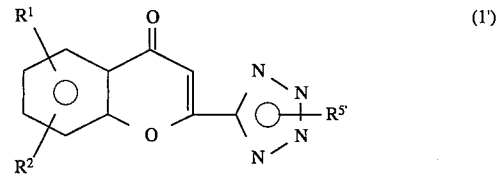

wherein $R^1$ and $R^2$ are the same or different and are a hydrogen atom, a hydroxy group, a halogen atom, a $C_1$–$C_{20}$ alkyl group, a $C_1$–$C_{20}$ alkoxy group, an $R^3$CONH group or a nitro group, in which $R^3$ is a $C_1$–$C_{20}$ alkyl group optionally substituted with an aryl group, or a phenyl group optionally substituted with $R^4$; $R^4$ is a $C_1$–$C_{20}$ alkyl group optionally substituted with an aryl group, or a $C_1$–$C_{20}$ alkoxy group optionally substituted with an aryl group; $R^{5'}$ is an alkyl or alkenyl group optionally substituted with an electron withdrawing group, an alkyl group substituted with 1 to 3 aryl groups, an alkoxycarbonyl group optionally substituted with an aryl group, an aryloxycarbonyl group, an alkoxymethyl group, a trialkyl tin group, a triaryl tin group or a trialkylsilyl group, in which the term "aryl group" or "aryl" means a phenyl group optionally substituted with a group selected from an alkyl group, an alkoxy group or a halogen atom, can be obtained.

The treatment temperature is usually 200° C. or lower, preferably 0° to 150° C. or up to the boiling point of the solvent. The proceeding of the reaction can readily be monitored by an analytical method such as liquid chromatography. Usually, disappearance of diketone compound (4) can be considered as the end point of the reaction.

After completion of the reaction, for example, the reaction mixture is washed with water and subjected to phase separation, and the desired 2-(tetrazol-5-yl)-4-oxo-4H-benzopyran (1) can be obtained from the organic layer.

In the case where crystals with good filtration properties cannot be obtained using the ordinary crystallization method by cooling or by addition of a solvent with poor solubility, when 2-(tetrazol-5-yl)-4-oxo-4H-benzopyran (1) is isolated from the reaction mixture, a solution or suspension obtained by dissolving or suspending the compound in an organic solvent immiscible with water is poured into water, and the organic solvent is removed by evaporation under stirring, which makes it possible to obtain large particle size crystals with good filtration properties.

As such an organic solvent immiscible with water, any organic solvent can be used, so long as it fall into the phase-separated state from water, when mixed with water, and there can be mentioned solvents such as hydrocarbons, halogenated hydrocarbons, ethers, water-insoluble ketones and nitriles, typical examples of which are those containing about 1 to 10 carbon atoms, such as hexane, benzene, toluene, xylene, dichloroethane, dichloromethane, chlorobenzene, dichlorobenzene, diethyl ether, t-butyl methyl ether and methyl isobutyl ketone.

The temperature at which an organic solvent is mixed is not particularly limited. For example, it can be conveniently selected within the range of from room temperature to the boiling point.

The concentration of 2-(tetrazol-5-yl)-4-oxo-4H-benzopyran (1) to an organic solvent is also not particularly limited. For example, it can be conveniently selected within the range of from 0.1% to 90% by weight. As the suspension, preferred is a suspension having flowability.

The solution or suspension thus obtained is gradually poured into water which is being stirred, and while stirring is continued so as to maintain the state that the poured solution or suspension is dispersed in water, preferably in liquid drop form, the organic solvent is removed by evaporation. As the stirring blade, there can be used any blade which is usually used, such as anchor blade, puddle blade, turbine blade, retreated blade or Brumagin blade.

The amount of water is not particularly limited, but selected such that water remains in the system when the removal of the organic solvent is completed, in the case where the organic solvent used forms an azeotropic mixture with water.

The temperature of the system is kept above the temperature at which the organic solvent can be removed by evaporation. For example, the boiling point of the organic solvent, or the azeotropic point in the case where the organic solvent used forms an azeotropic mixture with water, can be applied.

The removal of the organic solvent can be carried out either under increased pressure or under reduced pressure, and it is preferably carried out under reduced pressure, when the organic compound used is thermally unstable.

To maintain the state that the solution or suspension is dispersed in water, dispersing agents such as water-soluble cellulose esters can be used.

The particles grown by crystallization are deposited in water remaining after the removal of the organic solvent. The deposited particles can readily be collected by, for example, filtration.

In the case of 2-(tetrazol-5-yl)-4-oxo-4H-benzopyran (1) wherein $R^5$ is protected with an appropriate group as an alkyl group substituted with a phenyl group, such as benzyl, benzhydryl, 3-nitrobenzyl or 3-aminobenzyl group, the conversion of $R^5$ into a hydrogen atom can be carried out, if necessary, as described below.

That is, the compound is hydrogenated in the presence of a reduction catalyst such as palladium-carbon, palladium acetate, palladium oxide, platinum-carbon and Raney nickel in a solvent inert to the reaction to give 2-(tetrazol-5-yl)-4-oxo-4H-benzopyran (1) wherein $R^{5'}$ has been eliminated, i.e., $R^5$ is a hydrogen atom.

The reaction temperature is usually from 0° to 150° C., and as to the hydrogen pressure, the hydrogenation can be effected either under atmospheric pressure or under increased pressure. The proceeding of the reaction can readily be monitored by an analytical method such as liquid chromatography. Usually, disappearance of 2-(tetrazol-5-yl)-4-oxo-4H-benzopyran (1) wherein $R^5$ is not a hydrogen atom can be considered as the end point of the reaction.

In the case of an alkoxycarbonyl group, a phenoxycarbonyl group or an ethyl group with an electron withdrawing group, hydrolysis under acidic or alkaline conditions gives 2-(tetrazol-5-yl)-4-oxo-4H-benzopyran (1) wherein $R^5$ is a hydrogen atom. As the acid or alkali used, there can be mentioned hydrochloric acid and aqueous solutions of sodium hydroxide, potassium carbonate or the like.

According to the production process of the present invention, the reaction can be allowed to proceed with high efficiency by using an industrially favorable solvent which cannot be employed in the conventional process, whereby 2-(tetrazol-5-yl)-4-oxo-4H-benzopyran (1) can be obtained in an industrially favorable manner. Further, large crystals with good filtration properties can be obtained employing the particular crystallization method.

The present invention will be further illustrated by the following example; however, the present invention is not limited to these examples.

EXAMPLE 1

To a mixture of 1.00 g (7.34 mmol) of 2-hydroxyacetophenone, 8.47 g (22.0 mmol) of ethyl N-trityl-tetrazol-5-carboxylate and 20 ml of toluene was added 4.25 g (22.0 mmol) of 28% sodium methylate/methanol solution at room temperature, and the reaction was allowed to proceed at 50° C. for 1 hour.

To the reaction mixture was added dropwise 2.20 g (22.0 mol) of concentrated sulfuric acid at 50° C., and the reaction mixture was warmed to 60° C. and kept at the same temperature for 5 hours. After completion of the reaction, water and hexane were poured into the reaction mixture, which was filtered to give 1.5 g of 2-(1H-tetrazol-5-yl)-4-oxo-4H-benzopyran. Yield, 93%.

EXAMPLE 2

The reaction was effected according to Example 1, except that 3-[4-(4-phenyl-1-butoxy)benzoyl]amino-2-hydroxyacetophenone was used as the starting material in place of 2-hydroxyacetophenone used in Example 1, which afforded 3.0 g of 8-[4-(4-phenylbutoxy)benzoyl]amino-2-(1H-tetrazol-5-yl)-4-oxo-4H-benzopyran. Yield, 85%.

EXAMPLE 3

The reaction was effected according to Example 2, except that N-benzyltetrazol-5-carboxylate was used in place of N-trityltetrazol-5-carboxylate used in Example 2 and purification was carried out by column chromatography, which afforded 3.7 g of 8-[4-(4-phenylbutoxy)benzoyl]amino-2-(N-benzyltetrazol-5-yl)-4-oxo-4H-benzopyran. Yield, 87%; m.p., 155°–158° C.

EXAMPLE 4

In 10 ml of ethanol was dissolved 0.5 g of 8-[4-(4-phenylbutoxy)benzoyl]amino-2-(N-benzyltetrazol-5-yl)-4-oxo-4H-benzopyran, to which 0.03 g of 5% Pd—C was added, and the mixture was stirred under hydrogen atmosphere at room temperature for 24 hours.

After completion of the reaction was confirmed, 1.62 g of 5% aqueous $NaHCO_3$ solution was added, and the reaction mixture was filtered. The filtrate was poured into 10% aqueous acetic acid, and the deposited solid was filtered out. The crystals obtained by filtration were washed with ethanol and then dried to give 8-[4-(4-phenylbutoxy)benzoyl]amino-2-(1H-tetrazol-5-yl)-4-oxo-4H-benzopyran.

EXAMPLE 5

In a 0.5 liter separable flask equipped with a stirrer having three retreated blades was placed 300 ml of water, which was adjusted to pH 2 by addition of phosphoric acid. While it was keeping at 55° C. and stirring at 1200 rpm, a suspension prepared by suspending 10 g of 8-[4-(4-phenyl-1-butoxy)benzoyl]amino-2-(tetrazol-5-yl)-4-oxo-4H-benzopyran in 150 ml of toluene was poured into the flask over about 60 minutes. At the same time, an azeotropic mixture of toluene and water was distilled off under reduced pressure (200 mmHg). The temperature in the system at this time was kept at 52°–56° C. After completion of dropwise addition, the removal of toluene was shortly completed, and crystals were deposited in the water. The separable flask was cooled, and the water was filtered. The crystals obtained were dried. The crystals having a mean particle size of 1.5 mm were obtained.

EXAMPLE 6

In a 0.5 liter separable flask equipped with a stirrer having three retreated blades was placed 300 ml of water, which was adjusted to pH 2 by addition of phosphoric acid, and the mixture was kept at 55° C. and stirred at 1200 rpm.

A hot solution of 10 g of 8-[4-(4-phenyl-1-butoxy)benzoyl]amino-2-(tetrazol-5-yl)-4-oxo-4H-benzopyran in 150 ml of ethanol-2% aqueous sodium hydrogencarbonate (1:2) (this solution was used while being kept at 70° C.), together with 200 ml of toluene, was added dropwise to the flask over about 1 hour. At the same time, an azeotropic mixture of toluene, ethanol and water was distilled off under reduced pressure (200 mmHg). As a result, crystals having a mean particle size of 1.2 mm were obtained.

EXAMPLE 7

To a solution of 1.01 g (2.50 mmol) of 3-[4-(4-phenyl-1-butoxy)benzoyl]-amino-2-hydroxyacetophenone and 0.669 g (3.12 mmol) of ethyl N-ethoxycarbonyltetrazol-5-carboxylate dissolved in 10 ml of toluene was added 1.45 g (7.5 mmol) of 28% sodium methylate/methanol solution at room temperature, and the mixture was kept at 40° C. for 5 hours. To the resulting reaction mixture was added dropwise 1.22 g (12.7 mmol) of methanesulfonic acid at 40° C., and the mixture was kept at 60° C. for 5 hours. Then, 5% aqueous sodium dihydrogenphosphate and toluene were poured into the reaction mixture, followed by phase separation, washing with water, and concentration under reduced pressure. The residue was recrystallized from toluene to give 1.1 g of 2-(N-ethoxycarbonyltetrazol-5-yl)-4-oxo-4H-benzopyran. Yield, 77%; m.p., 154°–157° C. (decomp.).

COMPARATIVE EXAMPLE 1

In 150 ml of ethanol-2% aqueous sodium hydrogencarbonate (1:2) was dissolved with heating 10 g of 8-[4-(4-phenyl-1-butoxy)benzoyl]amino-2-(tetrazol-5-yl)-4-oxo-4H-benzopyran. To the resulting solution was added dropwise 20 ml of 10% hydrochloric acid at 70° C. over about 30 minutes, thereby causing deposition of crystals. Fine crystals having a mean particle size of 0.1 mm or less were obtained.

REFERENCE EXAMPLE

In a mixture of 20 ml of dichloromethane and 3.4 g (33.6 mmol) of triethylamine was dissolved 1.50 g (10.6 mmol) of ethyl tetrazol-5-carboxylate, and 3.75 g (34.6 mmol) of ethyl chloroformate was added dropwise at 0° C. After stirring overnight at 0° C. to room temperature, water was added to the reaction mixture, followed by phase separation. Then, the dichloromethane layer was successively washed with 5% sodium dihydrogenphosphate solution, 5% sodium hydrogencarbonate solution and water, dried with magnesium sulfate, and concentrated, which afforded 1.42 g of ethyl N-ethoxycarbonyltetrazol-5-carboxylate. Yield, 63%.

We claim:

1. A process for producing a 2-(tetrazol-5-yl)-4-oxo-4H-benzopyran of general formula (1):

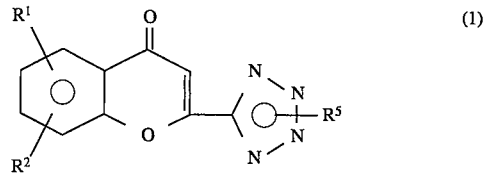

wherein $R^1$ and $R^2$ are the same or different and are a hydrogen atom, a hydroxy group, a halogen atom, a $C_1$–$C_{20}$ alkyl group, a $C_1$–$C_{20}$ alkoxy group, an $R^3CONH$ group or a nitro group, in which $R^3$ is a $C_1$–$C_{20}$ alkyl group optionally substituted with an aryl group, or a phenyl group optionally substituted with $R^4$; $R^4$ is a $C_1$–$C_{20}$ alkyl group optionally substituted with an aryl group, or a $C_1$–$C_{20}$ alkoxy group optionally substituted with an aryl group; $R^5$ is a hydrogen atom, an alkyl or alkenyl group optionally substituted with an electron withdrawing group, an alkyl group substituted with 1 to 3 aryl groups, an alkoxycarbonyl group optionally substituted with an aryl group, an aryloxycarbonyl group, an alkoxymethyl group, a trialkyl tin group, a triaryl tin group or a trialkylsilyl group, in which the term "aryl group" or "aryl" means a phenyl group optionally substituted with a group selected from an alkyl group, an alkoxy group or a halogen atom, characterized in that a hydroxyacetophenone of general formula (2):

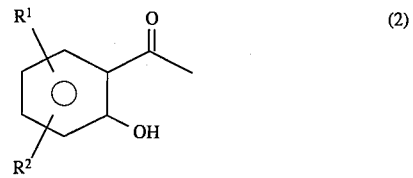

wherein $R^1$ and $R^2$ are as defined in the above general formula (1) is reacted with a tetrazole compound of general formula (3):

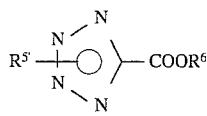
(3)

wherein $R^{5'}$ is $R^5$ which is not a hydrogen atom, $R^6$ is a lower alkyl group optionally substituted with a halogen atom, and $R^5$ is as defined in the general formula (1), in the presence of a base in a solvent composed mainly of at least one selected from hydrocarbons, halogenated hydrocarbons and alcohols, and the reaction mixture is then treated under acidic conditions.

2. A production process according to claim 1, wherein at least one of $R^1$ and $R^2$ is a nitro group or $R^3$CONH.

3. A process according to claim 1, wherein at least one of $R^1$ and $R^2$ is an $R^3$CONH group and $R^3$ is a phenylbutoxyphenyl group.

4. A process according to claim 1, wherein the solvent consists essentially of at least one selected from hydrocarbons, halogenated hydrocarbons and alcohols.

5. A process according to claim 1, wherein the solvent is an aromatic hydrocarbon.

6. A process according to claim 1, wherein the solvent is an aromatic halogenated hydrocarbon.

7. A process according to claim 1, wherein the solvent is toluene, xylene, monochlorobenzene or dichlorobenzene.

8. A process according to claim 1, wherein the solvent is an alcohol.

9. A process according to claim 8, wherein the alcohol is methanol, ethanol or isopropanol.

10. A process according to claim 1, wherein the base is an alkali metal alcoholate or an alcohol solution thereof.

11. A production process according to claim 1, wherein $R^5$ and $R^{5'}$ are both a benzyl group, a benzhydryl group or an alkoxycarbonyl group.

12. A process according to claim 1, wherein $R^{5'}$ is a 4-methoxybenzyl group, a trityl group or a methoxymethyl group, and $R^5$ is a hydrogen atom.

13. A process according to claim 1, wherein the electron withdrawing group is a cyano group, a methoxycarbonyl group or an ethoxycarbonyl group.

14. A process according to claim 1, wherein the 2-(tetrazol-5-yl)-4-oxo-4H-benzopyran (1) obtained is further dissolved or suspended in an organic solvent immiscible with water, and the resulting solution or suspension is poured into water, and the organic solvent is removed by evaporation to cause crystallization.

15. A process according to claim 1, wherein the resulting 2-(tetrazol-5-yl)-4-oxo-4H-benzopyran (1) in which $R^5$ is a benzyl group or a benzhydryl group is further reduced to convert $R^5$ into a hydrogen atom.

16. A 2-(tetrazol-5-yl)-4-oxo-4H-benzopyran of general formula (1'):

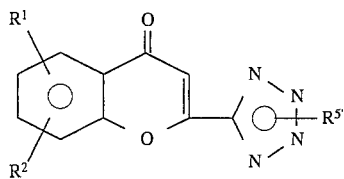
(1')

wherein $R^1$ and $R^2$ are the same or different and are a hydrogen atom, a hydroxy group, a halogen atom, a $C_1$–$C_{20}$ alkyl group, a $C_1$–$C_{20}$ alkoxy group, an $R^3$CONH group or a nitro group, in which $R^3$ is a $C_1$–$C_{20}$ alkyl group optionally substituted with an aryl group, or a phenyl group optionally substituted with $R^4$; $R^4$ is a $C_1$–$C_{20}$ alkyl group optionally substituted with an aryl group, or a $C_1$–$C_{20}$ alkoxy group optionally substituted with an aryl group; $R^{5'}$ is an alkyl or alkenyl group optionally substituted with an electron withdrawing group, an alkyl group substituted with 1 to 3 aryl groups, an alkoxycarbonyl group optionally substituted with an aryl group, an aryloxycarbonyl group, an alkoxymethyl group, a trialkyl tin group, a triaryl tin group or a trialkylsilyl group, in which the term "aryl group" or "aryl" means a phenyl group optionally substituted with a group selected from an alkyl group, an alkoxy group or a halogen atom.

17. A process for producing crystals of 2-(tetrazol-5-yl)-4-oxo-4H-benzopyran (4), characterized in that a 2-(tetrazol-5-yl)-4-oxo-4H-benzopyran of general formula (1'):

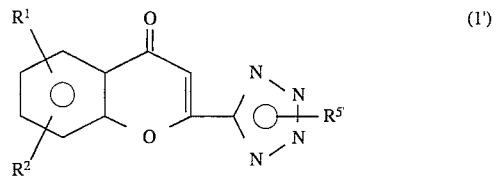
(1')

wherein $R_1$ and $R^2$ are the same or different and are a hydrogen atom, a hydroxy group, a halogen atom, a $C_1$–$C_{20}$ alkyl group, a $C_1$–$C_{20}$ alkoxy group, an $R^3$CONH group or a nitro group, in which $R^3$ is a $C_1$–$C_{20}$ alkyl group optionally substituted with an aryl group, or a phenyl group optionally substituted with $R^4$; $R^4$ is a $C_1$–$C_{20}$ alkyl group optionally substituted with an aryl group, or a $C_1$–$C_{20}$ alkoxy group optionally substituted with an aryl group; $R^{5'}$ is an alkyl or alkenyl group optionally substituted with an electron withdrawing group, an alkyl group substituted with 1 to 3 aryl groups, an alkoxycarbonyl group optionally substituted with an aryl group, an aryloxycarbonyl group, an alkoxymethyl group, a trialkyl tin group, a triaryl tin group or a trialkylsilyl group, in which the term "aryl group" or "aryl" means a phenyl group optionally substituted with a group selected from an alkyl group, an alkoxy group or a halogen atom, is dissolved or suspended in an organic solvent immiscible with water or its mixture with water, and the resulting solution or suspension, together with an organic solvent immiscible with water, is poured into water, and the organic solvent is removed by evaporation under stirring to give crystals.

* * * * *